(12) United States Patent
Nochumson et al.

(10) Patent No.: US 7,732,216 B2
(45) Date of Patent: Jun. 8, 2010

(54) SYSTEM AND METHOD FOR TESTING CHROMATOGRAPHY MEDIA AND DEVICES

(75) Inventors: Samuel Nochumson, Pensacola, FL (US); Peter Levison, Havant (GB)

(73) Assignee: Pall Corporation, Port Washington, NY (US)

( * ) Notice: Subject to any disclaimer, the term of this patent is extended or adjusted under 35 U.S.C. 154(b) by 0 days.

(21) Appl. No.: 12/096,033

(22) PCT Filed: Nov. 17, 2006

(86) PCT No.: PCT/US2006/061009
§ 371 (c)(1),
(2), (4) Date: Jun. 4, 2008

(87) PCT Pub. No.: WO2007/120272
PCT Pub. Date: Oct. 25, 2007

(65) Prior Publication Data
US 2008/0299672 A1   Dec. 4, 2008

Related U.S. Application Data

(60) Provisional application No. 60/742,567, filed on Dec. 6, 2005, provisional application No. 60/817,349, filed on Jun. 30, 2006.

(51) Int. Cl.
*G01N 30/02* (2006.01)
(52) U.S. Cl. .................................... 436/161; 436/162

(58) Field of Classification Search ................. 436/161; 210/656
See application file for complete search history.

(56) References Cited

U.S. PATENT DOCUMENTS

| 4,895,808 | A | 1/1990 | Romer |
| 6,435,012 | B2 | 8/2002 | Maikner |
| 2002/0166816 | A1* | 11/2002 | Allen et al. ............. 210/656 |

FOREIGN PATENT DOCUMENTS

| WO | WO 01/11355 | 2/2001 |
| WO | WO 2005/015165 | 2/2005 |

OTHER PUBLICATIONS

Meyer et al. "Influence of leaks in the liquid chromatographic instrument on analytical results". J Chrom A, 1997, vol. 767, pp. 25-31.*
International Search Report for PCT/US2006/061009, filed Nov. 17, 2006.
Written Opinion of the International Searching Authority for PCT/US2006/061009, filed Nov. 17, 2006.

(Continued)

*Primary Examiner*—Yelena G Gakh
*Assistant Examiner*—David Weisz
(74) *Attorney, Agent, or Firm*—Leydig, Voit & Mayer, Ltd.

(57) ABSTRACT

Methods for testing the chromatography type and/or the integrity of a chromatography membrane or monolith, preferably, for testing the chromatography type and integrity of a chromatography device comprising a chromatography membrane or chromatography monolith while the membrane or monolith is sealed in a housing, are disclosed.

18 Claims, 6 Drawing Sheets

OTHER PUBLICATIONS

BIA Separations CIM® Disk Monolithic Columns, http://www.biaseparations.com/documents/Products/cimdisks.asp, 4 pages, printed from Internet Jul. 22, 2005.

Coffinier, Y. et al., *Journal of Membrane Science*, 208:13-22 (2002).

Engelhardt, H. et al., *Journal of Chromatography*, 544(1):371-379 (1991).

Handbook of Process Chromatography, Gail Sofer and Lars Hagel, Academic Press, Chapter 15, pp. 361-365 (1997).

Jungbauer, A. et al., *J. Sep. Sci*, 27:767-778 (2004).

Kele, M. et al., *Journal of Chromatography A*, 830(1):41-54 (1999).

Leinweber, F. C. et al., *Journal of Chromatography A*, 1006:207-228 (2003).

Martin del Valle, E. et al. *Biotechnol. Prog.*, 19:921-927 (2003).

MBI HyperCel™, Mixed-mode sorbent for direct capture of antibodies, Pall Life Sciences, Product Note, pp. 1-8 (2004).

Neue, U. D., et al., *Journal of Chromatography A*, 489(1):101-116 (1999).

Rozanas, C., *Life Science News I*, pp. 1-4 (1998).

Stella, C. et al., *Chromatographia Supplement*, 53:S-132-S140 (2001).

Svec, F. et al., Porous Monoliths: Emerging Stationary Phases for HPLC and Related Methods, http://www.lcgcelectronic.com/062304/Pag_15.asp, 4 pages, printed from Internet Jun. 27, 2005.

Zöchling, A. et al., *J. Sep. Sci.*, 27:819-827 (2004).

International Preliminary Report on Patentability for PCT/US2006/061009 filed Nov. 17, 2006.

* cited by examiner

SYSTEM AND METHOD FOR TESTING CHROMATOGRAPHY MEDIA AND DEVICES

CROSS-REFERENCE TO RELATED APPLICATIONS

This application claims the benefit of U.S. Provisional Application Nos. 60/742,567, filed Dec. 6, 2005, and 60/817,349, filed Jun. 30, 2006, which are each incorporated by reference.

BACKGROUND OF THE INVENTION

The invention relates to a system and method for testing chromatography media and devices, particularly chromatography devices including membranes and monoliths. More particularly, the invention relates to testing the integrity and/or chromatography type of chromatography membranes and monoliths sealed in a housing.

Chromatography devices including beads in the form of columns or packed beds can be integrity tested by, for example, using the height equivalent to a theoretical plate (HETP) method. The HETP method involves introducing an analyte into the column under non-binding conditions, washing the analyte through the column, and detecting the analyte in the column effluent. The HETP is then calculated using known mathematical equations. The HETP measurement demonstrates bed integrity (packing), and can provide an indication as to bed to bed reproducibility.

However, the HETP method does not show the sealing integrity of a sealed unit, e.g., a capsule, or a housing (that can be re-usable) including chromatography media sealed therein, or a monolith containing a polymerized gel or inorganic material (e.g., a silica-based material) sealed therein. Moreover, while the chromatography type of the beads in a column can be determined relatively easily, e.g., by analyzing a few beads, there is an unmet need in the art for a method for determining the chromatography type of the chromatography membranes or monoliths sealed in a housing, e.g., a chromatography capsule.

The present invention provides for ameliorating at least some of the disadvantages of the prior art. These and other advantages of the present invention will be apparent from the description as set forth below.

BRIEF SUMMARY OF THE INVENTION

An embodiment of the invention provides a method for testing the integrity of a chromatography membrane sealed in a housing comprising obtaining a chromatography device comprising a housing and having one or more membranes to be tested sealed in the housing; obtaining a selected analyte that will bind to the membrane(s) under standard binding conditions; placing the analyte in contact with the membrane(s) under standard binding conditions; eluting the analyte from the membrane(s) with an elution fluid to form an eluate containing the eluted analyte, the eluted analyte having a measurable concentration in the eluate; measuring a change in the concentration of the eluted analyte in the eluate over a period of time to provide an elution pattern for the tested membrane(s); comparing the elution pattern for the tested membrane(s) to a reference elution pattern for a membrane of known integrity; and determining the integrity of the tested membrane(s).

An embodiment of the invention provides a method for testing the integrity of a chromatography monolith sealed in a housing comprising obtaining a chromatography device comprising a housing and having one or more monoliths to be tested sealed in the housing; obtaining a selected analyte that will bind to the monolith(s) under standard binding conditions; placing the analyte in contact with the monolith(s) under standard binding conditions; eluting the analyte from the monolith(s) with an elution fluid to form an eluate containing the eluted analyte, the eluted analyte having a measurable concentration in the eluate; measuring a change in the concentration of the eluted analyte in the eluate over a period of time to provide an elution pattern for the tested monolith(s); comparing the elution pattern for the tested monolith(s) to a reference elution pattern for a monolith of known integrity; and determining the integrity of the tested monolith(s).

A method for testing the type and integrity of a chromatography membrane sealed in a housing according to another embodiment of the invention comprises obtaining a selected analyte, the analyte being capable of binding, under standard binding conditions, to a membrane having a specified chromatography type; obtaining one or more membrane(s) having a chromatography type to be tested to determine whether the membrane(s) has/have the specified chromatography type; placing the analyte in contact with the membrane(s) under standard binding conditions wherein the analyte binds to the membrane(s) if the membrane(s) has/have the specified chromatography type; contacting the membrane(s) with an elution fluid to form an eluate, wherein the eluate contains the eluted analyte if the membrane(s) to be tested has/have the specified chromatography type, the eluted analyte having a measurable concentration in the eluate; measuring a change in the concentration of the eluted analyte in the eluate over a period of time to provide an elution pattern for the tested membrane(s); comparing the elution pattern for the tested membrane(s) to a reference elution pattern for a membrane of known integrity; and determining the integrity of the membrane(s) and whether the membrane(s) has/have the specified chromatography type.

A method for testing the type and integrity of a chromatography monolith sealed in a housing according to another embodiment of the invention comprises obtaining a selected analyte, the analyte being capable of binding, under standard binding conditions, to a monolith having a specified chromatography type; obtaining one or more monolith(s) having a chromatography type to be tested to determine whether the monolith(s) has/have the specified chromatography type; placing the analyte in contact with the monolith(s) under standard binding conditions wherein the analyte binds to the monolith(s) if the monolith(s) has/have the specified chromatography type; contacting the monolith(s) with an elution fluid to form an eluate, wherein the eluate contains the eluted analyte if the monolith(s) to be tested has/have the specified chromatography type, the eluted analyte having a measurable concentration in the eluate; measuring a change in the concentration of the eluted analyte in the eluate over a period of time to provide an elution pattern for the tested monolith(s); comparing the elution pattern for the tested monolith(s) to a reference elution pattern for a monolith of known integrity; and determining the integrity of the monolith(s) and whether the monolith(s) has/have the specified chromatography type.

A method for testing the integrity of a chromatography device including at least one chromatography medium according to an embodiment of the invention comprises obtaining a chromatography device comprising a housing comprising an inlet and an outlet and having at least one chromatography medium sealed in the housing; obtaining a selected analyte that will bind to the medium/media under standard binding conditions; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; and determining the integrity of the device.

In an embodiment, the method for testing the integrity of a chromatography device further comprises testing the chromatography type of the chromatography medium/media in the device, wherein, after passing the volume of non-analyte eluting fluid through the device, the method further comprises contacting the medium/media with an elution fluid to form an eluate, wherein the eluate contains the eluted analyte if the medium/media to be tested has/have the specified chromatography type, the eluted analyte having a measurable concentration in the eluate; analyzing the eluate to determine if the analyte is present; and, determining whether the medium/media has/have the specified chromatography type.

A method for testing the chromatography type of at least one chromatography medium sealed in a chromatography device according to another embodiment of the invention comprises obtaining a chromatography device comprising a housing comprising an inlet and an outlet and having at least one chromatography medium sealed in the housing; obtaining a selected analyte that will bind to the chromatography medium/media under standard binding conditions if the medium/media has the chromatography type to be tested; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; contacting the medium/media with an elution fluid to form an eluate, wherein the eluate contains the eluted analyte if the medium/media to be tested has/have the specified chromatography type, the eluted analyte having a measurable concentration in the eluate; analyzing the eluate to determine if the analyte is present; and, determining whether the medium/media has/have the specified chromatography type.

A method for testing the chromatography type of at least one chromatography medium sealed in a chromatography device according to yet another embodiment of the invention comprises obtaining a chromatography device comprising a housing comprising an inlet and an outlet and having at least one chromatography medium sealed in the housing; obtaining a selected analyte that will bind to the chromatography medium/media under standard binding conditions if the medium/media has the specified chromatography type to be tested; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; and determining whether the medium/media has/have the specified chromatography type.

In another embodiment, a method for testing the type of a chromatography membrane comprises obtaining a selected analyte, the analyte being capable of binding, under standard binding conditions, to a membrane having a specified chromatography type; obtaining one or more membranes having a chromatography type to be tested to determine whether the membrane(s) has/have the specified chromatography type; placing the analyte in contact with the membrane(s) under standard binding conditions wherein the analyte binds to the membrane(s) if the membrane(s) has/have the specified chromatography type; contacting the membrane(s) with an elution fluid to form an eluate, wherein the eluate contains the eluted analyte if the membrane(s) to be tested has/have the specified chromatography type, the eluted analyte having a measurable concentration in the eluate; analyzing the eluate to determine if the analyte is present; and, determining whether the membrane(s) has/have the specified chromatography type.

Preferably, embodiments of the method comprise testing the integrity and/or chromatography type of a chromatography medium or chromatography media sealed in a housing. Even more preferably, embodiments of the method comprise testing the integrity and the chromatography type of a plurality of chromatography membranes sealed in a chromatography capsule.

BRIEF DESCRIPTION OF THE SEVERAL VIEWS OF THE DRAWING(S)

FIG. 2 shows three elution patterns in a single graph. Membranes of known integrity are tested to provide the first pattern (the reference pattern), the membranes were punctured once and tested to provide the second pattern, and the membranes were punctured again and tested to provide the third pattern.

Figure 3A:
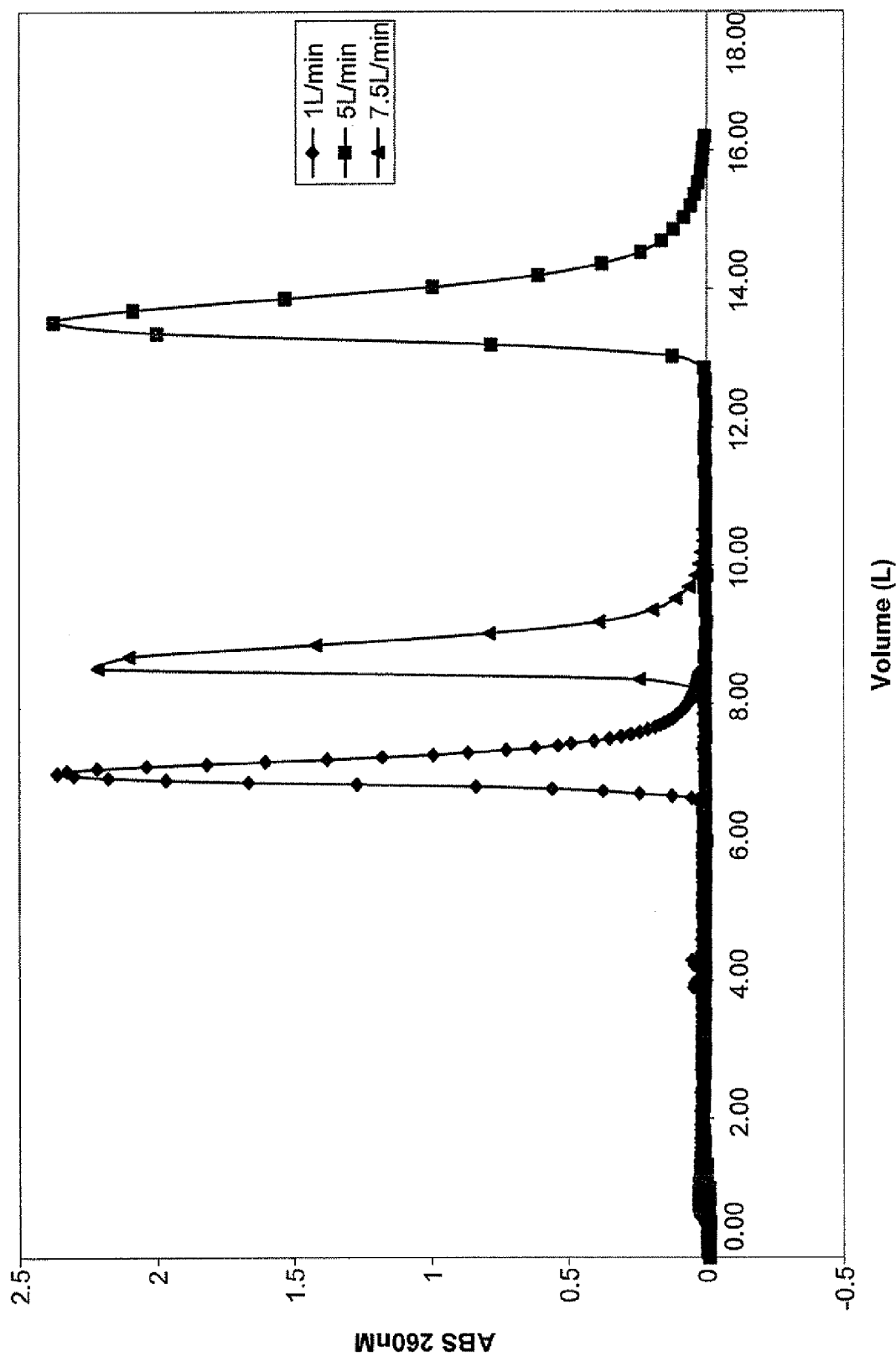
Figure 3B:
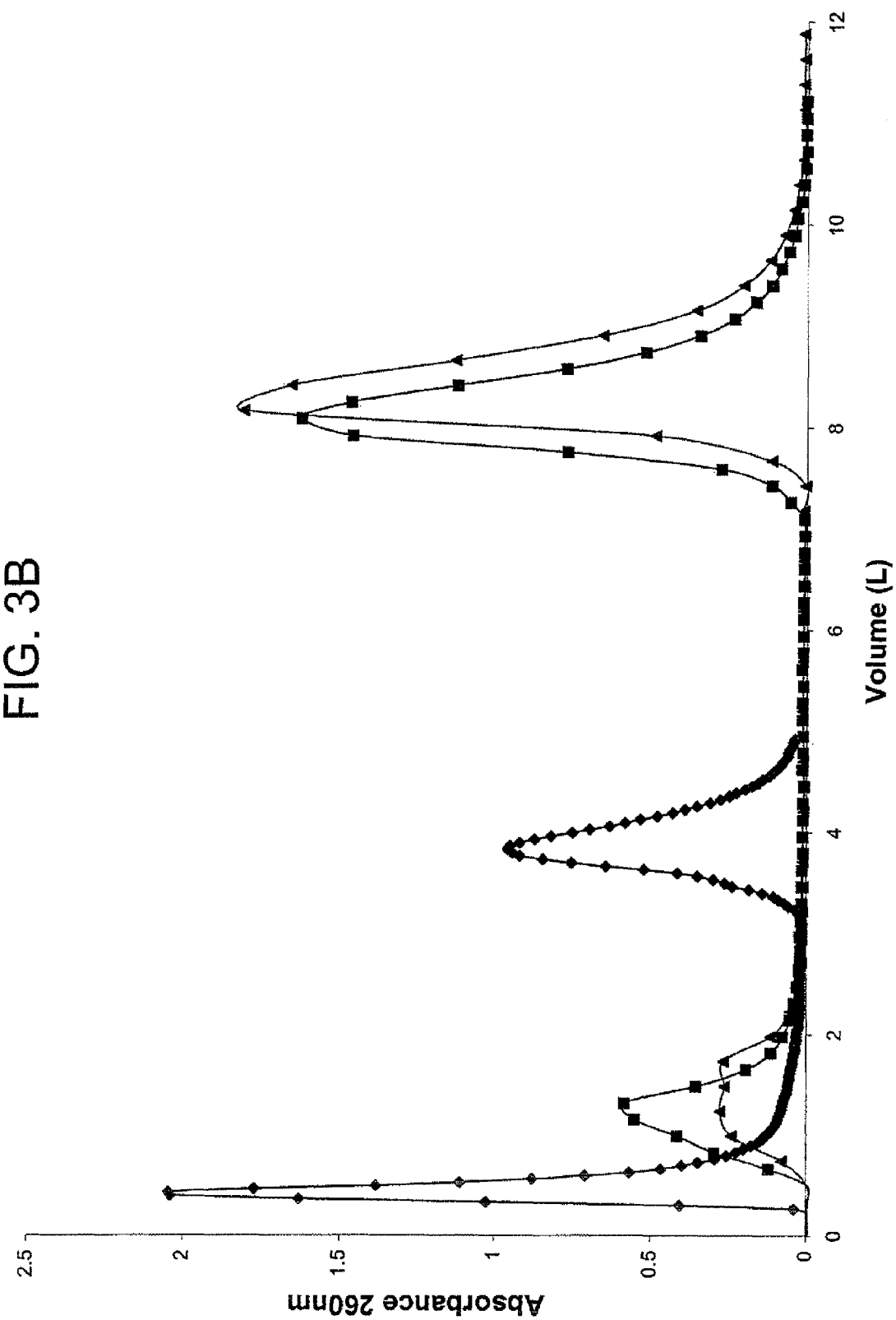
Figure 3C:
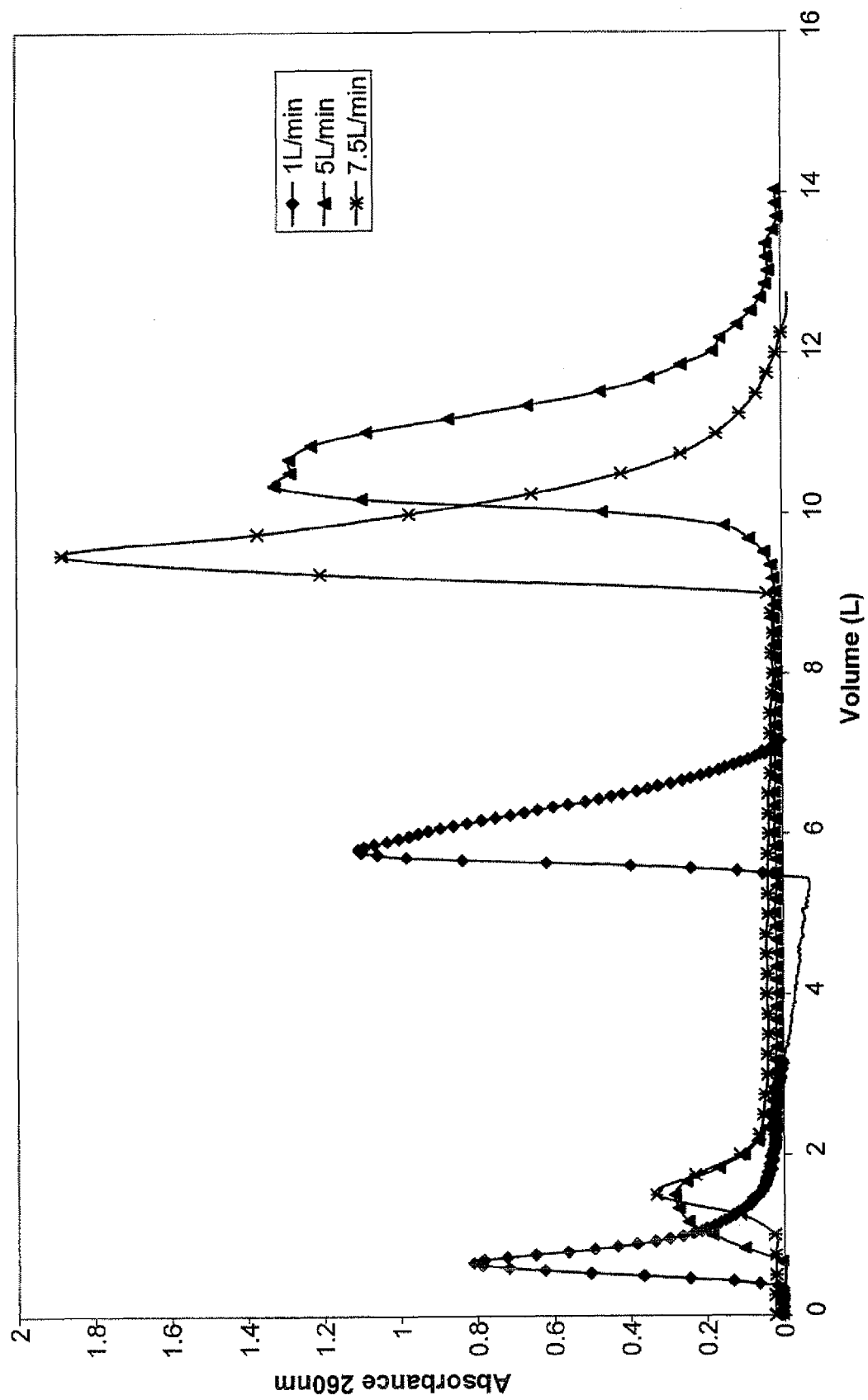

FIG. 3 shows three sets of elution patterns. Membranes of known integrity are tested at three different flow rates to provide the first pattern (the reference pattern; FIG. 3A), the membranes were punctured once and tested at the three flow rates to provide the second pattern (FIG. 3B), and the membranes were punctured again and tested at the three flow rates to provide the third pattern (FIG. 3C).

Figure 4:
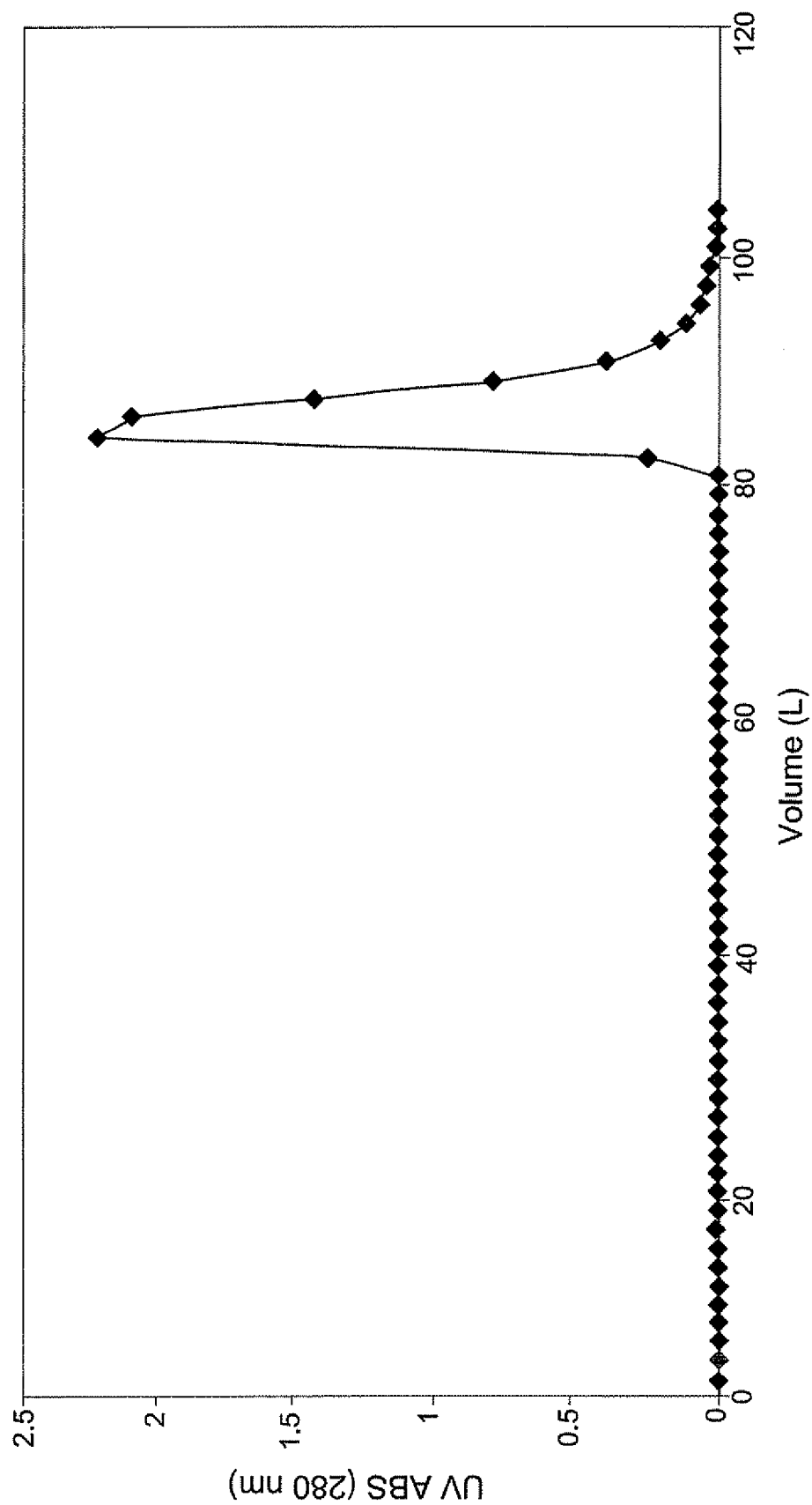

FIG. 4 shows the elution pattern from an integrity test and chromatography type test of a commercially available chromatography capsule

DETAILED DESCRIPTION OF THE INVENTION

An embodiment of the invention provides a method for testing the integrity of a chromatography membrane sealed in a housing comprising obtaining a chromatography device comprising a housing and having one or more membranes to be tested sealed in the housing; obtaining a selected analyte that will bind to the membrane(s) under standard binding conditions; placing the analyte in contact with the membrane(s) under standard binding conditions; eluting the analyte from the membrane(s) with an elution fluid to form an eluate containing the eluted analyte, the eluted analyte having a measurable concentration in the eluate; measuring a change in the concentration of the eluted analyte in the eluate over a period of time to provide an elution pattern for the tested membrane(s); comparing the elution pattern for the tested membrane(s) to a reference elution pattern for a membrane of known integrity; and determining the integrity of the tested membrane(s).

An embodiment of the invention provides a method for testing the integrity of a chromatography monolith sealed in a housing comprising obtaining a chromatography device comprising a housing and having one or more monoliths to be tested sealed in the housing; obtaining a selected analyte that will bind to the monolith(s) under standard binding conditions; placing the analyte in contact with the monolith(s) under standard binding conditions; eluting the analyte from the monolith(s) with an elution fluid to form an eluate containing the eluted analyte, the eluted analyte having a measurable concentration in the eluate; measuring a change in the concentration of the eluted analyte in the eluate over a period of time to provide an elution pattern for the tested monolith(s); comparing the elution pattern for the tested monolith(s) to a reference elution pattern for a monolith of known integrity; and determining the integrity of the tested monolith(s).

A method for testing the type and integrity of a chromatography membrane sealed in a housing according to another embodiment of the invention comprises obtaining a selected analyte, the analyte being capable of binding, under standard binding conditions, to a membrane having a specified chromatography type; obtaining a chromatography device comprising a housing and one or more chromatography membranes to be tested sealed in the housing, the one or more membrane(s) having a chromatography type to be tested to determine whether the membrane(s) has/have the specified chromatography type; placing the analyte in contact with the membrane(s) under standard binding conditions wherein the analyte binds to the membrane(s) if the membrane(s) has/have the specified chromatography type; contacting the membrane(s) with an elution fluid to form an eluate, wherein the eluate contains the eluted analyte if the membrane(s) to be tested has/have the specified chromatography type, the eluted analyte having a measurable concentration in the eluate; measuring a change in the concentration of the eluted analyte in the eluate over a period of time to provide an elution pattern for the tested membrane(s); comparing the elution pattern for the tested membrane(s) to a reference elution pattern for a membrane of known integrity; and determining the integrity of the membrane(s) and whether the membrane(s) has/have the specified chromatography type.

A method for testing the type and integrity of a chromatography monolith sealed in housing according to another embodiment of the invention comprises obtaining a selected analyte, the analyte being capable of binding, under standard binding conditions, to a monolith having a specified chromatography type; obtaining a chromatography device comprising a housing and one or more chromatography monoliths to be tested sealed in the housing, the one or more monolith(s) having a chromatography type to be tested to determine whether the monolith(s) has/have the specified chromatography type; placing the analyte in contact with the monolith(s) under standard binding conditions wherein the analyte binds to the monolith(s) if the monolith(s) has/have the specified chromatography type; contacting the monolith(s) with an elution fluid to form an eluate, wherein the eluate contains the eluted analyte if the monolith(s) to be tested has/have the specified chromatography type, the eluted analyte having a measurable concentration in the eluate; measuring a change in the concentration of the eluted analyte in the eluate over a period of time to provide an elution pattern for the tested monolith(s); comparing the elution pattern for the tested monolith(s) to a reference elution pattern for a monolith of known integrity; and determining the integrity of the monolith(s) and whether the monolith(s) has/have the specified chromatography type.

A method for testing the integrity of a chromatography device including at least one chromatography medium according to an embodiment of the invention comprises obtaining a chromatography device comprising a housing comprising an inlet and an outlet and having at least one chromatography medium sealed in the housing; obtaining a selected analyte that will bind to the chromatography medium/media under standard binding conditions; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; and determining the integrity of the device.

In an embodiment, the method for testing the integrity of a chromatography device further comprises testing the chromatography type of the chromatography medium/media in the device, wherein, after passing the volume of non-analyte eluting fluid through the device, the method further comprises contacting the medium/media with an elution fluid to form an eluate, wherein the eluate contains the eluted analyte if the medium/media to be tested has/have the specified chromatography type, the eluted analyte having a measurable concentration in the eluate; analyzing the eluate to determine if the analyte is present; and, determining whether the medium/media has/have the specified chromatography type.

A method for testing the chromatography type of at least one chromatography medium sealed in a chromatography device according to another embodiment of the invention comprises obtaining a chromatography device comprising a housing comprising an inlet and an outlet and having at least one chromatography medium sealed in the housing; obtaining a selected analyte that will bind to the chromatography medium/media under standard binding conditions if the medium/media has the chromatography type to be tested; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; contacting the medium/media with an elution fluid to form an eluate, wherein the eluate contains the eluted analyte if the medium/media to be tested has/have the specified chromatography type, the eluted analyte having a measurable concentration in the eluate; analyzing the eluate to determine if the analyte is present; and, determining whether the medium/media has/have the specified chromatography type.

A method for testing the chromatography type of at least one chromatography medium sealed in a chromatography device according to yet another embodiment of the invention comprises obtaining a chromatography device comprising a housing comprising an inlet and an outlet and having at least one chromatography medium sealed in the housing; obtaining a selected analyte that will bind to the chromatography medium/media under standard binding conditions if the medium/media has the specified chromatography type to be tested; preparing a liquid sample containing the analyte; passing a volume of the liquid sample into the device including placing an amount of the analyte in contact with the medium/media under standard binding conditions wherein the amount of analyte in the liquid sample placed in contact with the medium/media is less than the binding capacity of the medium/media; passing a volume of non-analyte eluting fluid through the device wherein the volume of non-analyte eluting fluid passed through the device is at least substantially equal to the volume of the liquid sample; determining the presence or absence of the analyte in liquid passing from the outlet of the device; and determining whether the medium/media has/have the specified chromatography type.

In another embodiment, a method for testing the type of a chromatography membrane comprises obtaining a selected analyte, the analyte being capable of binding, under standard binding conditions, to a membrane having a specified chromatography type; obtaining one or more membranes having a chromatography type to be tested to determine whether the membrane(s) has/have the specified chromatography type; placing the analyte in contact with the membrane(s) under standard binding conditions wherein the analyte binds to the membrane(s) if the membrane(s) has/have the specified chromatography type; contacting the membrane(s) with an elution fluid to form an eluate, wherein the eluate contains the eluted analyte if the membrane(s) to be tested has/have the specified chromatography type, the eluted analyte having a measurable concentration in the eluate; analyzing the eluate to determine if the analyte is present; and, determining whether the membrane(s) has/have the specified chromatography type.

Preferably, embodiments of the method comprise testing the integrity and/or chromatography type of a chromatography medium or chromatography media sealed in a housing. Even more preferably, embodiments of the method comprise testing the integrity of a chromatography capsule and testing the chromatography type of a plurality of chromatography membranes sealed in the chromatography capsule.

As used herein, "chromatography medium," "chromatography media" and "chromatography medium/media" refer to, in context, one or more chromatography membranes and/or one or more chromatography monoliths. A chromatography device can include any number of chromatography membranes or chromatography monoliths. A chromatography device can include a plurality (i.e., two or more) of the same type of media, or different types of media. Alternatively, or additionally, a chromatography device can include a plurality of the same type of media (e.g., membranes) wherein the media have different characteristics, e.g., chromatography types.

Embodiments of the invention can be utilized to determine breaches of the membrane or monolith (e.g., punctures, tears, and/or breaks) and/or breaches of the sealing points (e.g., the seal between the membrane or the monolith and one or more other components of the device). Thus, the user can determine the sealing integrity of a chromatography device and determine whether the chromatography device is defective and likely unfit for its intended purpose.

In contrast with the HETP measurement, that utilizes an analyte that does not bind or adsorb to the chromatography bead, in accordance with embodiments of the invention, the selected analyte binds or adsorbs to the medium/media to be tested, and is selectively desorbed or eluted.

In accordance with an embodiment for testing the integrity of chromatography medium/media according to the invention, the medium/media having the selected analyte bound thereto is/are washed (e.g., with a non-analyte eluting fluid that does not elute the analyte, for example, a non-analyte eluting fluid such as water or an equilibrium buffer) from the medium/media being tested, and the presence or absence of a detectable concentration of the analyte in the wash over a period of time is measured. In accordance with this embodiment, if the integrity of the medium/media being tested has not been breached, there will be little or no analyte detected in the wash.

In accordance with an embodiment for testing the chromatography type of a chromatography membrane or monolith according to the invention, the bound selected analyte is eluted from the membrane or monolith being tested, and the change in the concentration of the analyte in the eluate over a period of time is measured (or the presence or absence of a detectable peak of the analyte is determined) to provide an elution pattern.

In a more preferred embodiment, the elution pattern is compared to a reference elution pattern for a membrane or monolith of known chromatography type and integrity. For example, a selected analyte is bound to and eluted from one or more membranes or monoliths (or filter elements containing the membranes or monoliths) of known chromatography type and integrity to determine the elution pattern, and this provides the reference elution pattern. If desired, when testing a chromatography device including a plurality of media (e.g., a capsule including a number of membrane layers) the reference elution pattern utilized can, in some embodiments, be prepared using the same or a similar number of media utilized in the device. Alternatively, or additionally, if desired, a selected analyte can be bound to and eluted from the several membranes or monoliths of known integrity and of the same known chromatography type to provide a range of reference elution patterns. In some embodiments, a reference pattern is provided by the manufacturer and/or supplier of the membrane, monolith, or chromatography device. For example, it can be provided as an insert and/or as part of the instructions supplied with the membrane, monolith, or chromatography device.

A wide variety of chromatography devices including one or more membranes or monoliths (e.g., polymerized gels, silica columns, ceramics, graphitized carbon) can be utilized in accordance with embodiments of the invention. In some embodiments, the chromatography device, i.e., comprising the housing and the chromatography medium or chromatography media sealed therein, is a preassembled device, e.g., wherein the medium/media is/are sealed in the housing by the device manufacturer. In some other embodiments, the medium/media is/are sealed in the housing by the end user. The devices can be suitable for treating a variety of fluids, e.g., to purify and/or concentrate one or more desired materials present in the fluids. For example, the devices can be suitable for treating process fluids such as fluids used in the biopharmaceutical industry, e.g., fluids including desirable material such as proteinaceous material, for example, antibodies (e.g., monoclonal antibodies), or recombinant proteins such as growth factors.

The chromatography devices (e.g., capsules), the housings, membranes, and/or monoliths can have any suitable configuration, including, but not limited to, configurations known in the art. For example, the membranes can be one or more of the following forms: planar, pleated, hollow cylindrical, stacked, and spiral wound. Illustratively, in one embodiment, the membrane(s) can be in the form of a hollow, generally cylindrical, pleated element. The monoliths can be one or more of the following forms: disk, tube, and column.

Figure 1:
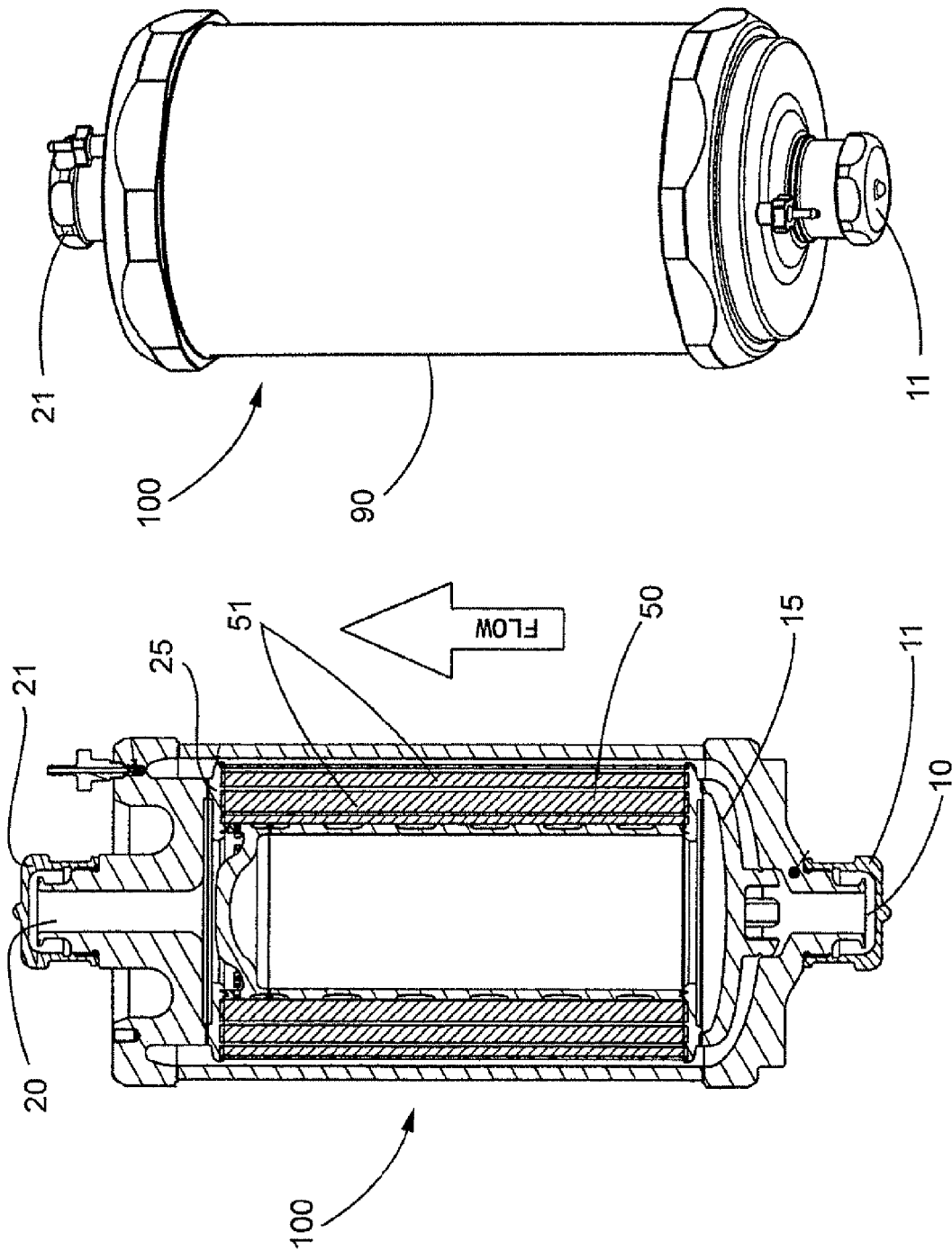
FIG. 1 shows isometric and cross-sectional views of an illustrative sealed chromatography capsule including chromatography membranes that can be tested in accordance with an embodiment of the invention.

FIG. 1 shows an isometric and a cross-sectional view of an illustrative sealed chromatography device including a plurality of membranes that can be tested in accordance with an embodiment of the invention. In this Figure, exemplary chromatography device 100 comprises a housing 90 including end caps 15 and 25, the housing having an inlet 10, and an outlet 20, and defining a fluid flow path between the inlet and the outlet, the device having a fluid treatment element 50 comprising a plurality of membranes 51 (shown in the Figure as forming a hollow generally cylindrical element) sealed in the housing across the fluid flow path. The illustrated device also includes protective caps 11 and 21, covering the inlet and outlet, respectively, wherein the caps are removed before use.

An illustrative sealed chromatography device including a monolith (not shown) that can be tested in accordance with an embodiment of the invention comprises at least one monolith matrix disk sealed in a housing comprising a fitting ring. If desired, a plurality of chromatography devices (e.g., monolith disks sealed in fitting rings) can be sealed in an additional housing, e.g., a column, before use in chromatography.

The membrane(s) or monolith(s) can have any desired characteristics, e.g., chromatography type, and a variety of membranes and monoliths (and chromatography devices such as chromatography capsules), including commercially available membranes and monoliths (and commercially available chromatography devices containing such membranes or monoliths), can be tested according to the invention. For example, a variety of ion-exchange membranes and/or monoliths, including a variety of commercially available ion-exchange and/or monoliths, can be tested according to the invention. The membrane(s) or monolith(s) (or chromatography device containing such membrane(s) or monolith(s)) can be tested to determine whether, for example, the membrane or monolith is a charged membrane or charged monolith, e.g., a positively charged or a negatively charged membrane or monolith.

Alternatively, or additionally, the membrane or monolith can be tested to determine whether the chromatography type of the membrane or monolith is one of more of the following: a hydrophobic interactive chromatography (HIC) membrane or monolith, an affinity chromatography (e.g., immobilized metal affinity chromatography (IMAC)) membrane or monolith, a biospecific (e.g., immobilized Protein A) affinity chromatography membrane or monolith, a hydrophobic charge induction chromatography (HCIC) membrane or monolith, and a thiophilic chromatography (TC) membrane or monolith. A variety of such membranes and/or monoliths (and chromatography devices including such membranes and/or monoliths), including a variety of commercially available membranes and/or monoliths (and chromatography devices including such membranes and/or monoliths), can be so tested according to the invention.

In accordance with the invention, a variety of analytes are suitable for use in testing the membrane(s) or monolith(s). Preferably, the analyte is essentially non-toxic, and more preferably, the analyte, once eluted from the membrane or monolith, can be easily separated from the elution fluid (e.g., the equilibration buffer) and/or the fluid to be treated (e.g., the process fluid).

In a preferred embodiment, the analyte is utilized as a "pulse," for example, a small portion (e.g., small volume and/or low concentration) of analyte sufficient to provide a detectable signal, wherein the amount placed in contact with the chromatography medium or media (i.e., the membrane(s) or monolith(s)) is less than the binding capacity of the membrane(s) or monolith(s). The use of a pulse provides a time saving, allowing the test to be carried out more quickly. In one embodiment, the chromatography medium/media having the analyte in the pulse bound thereto is washed (e.g., with a non-analyte eluting fluid such as water or an equilibrium buffer) from a device containing the medium or media sealed therein, and the absence of a detectable analyte in the wash reflects the integrity of the device. Preferably, the pulse is subsequently eluted from the medium or media, providing an elution pattern reflecting the chromatography type of the medium or media.

Suitable analytes, that can be natural or synthetic, include, for example, small molecules such as purines, pyrimidines, nucleosides (e.g., adenosine) or nucleotides such as mononucleotides (e.g., adenosine monophosphate (AMP), adenosine diphosphate (ADP), and adenosine triphosphate (ATP)), nucleic acids (e.g., RNA such as soluble RNA, or DNA such as plasmid DNA), mid-size molecules such as cytochrome c, or the analytes can be large molecules including macromolecules such as proteins (e.g., bovine serum albumin (BSA), an enzyme such as lysozyme or ribonuclease A, or an immunoglobulin or antibody such as IgG, a macroglobulin (e.g., $\alpha_2$-macroglobulin) or an antibody fragment), peptides, and polymers.

In one embodiment, the analyte is a small molecule as, once it is eluted, it can be more easily separated from the elution fluid and/or the fluid to be treated. Illustratively, an exemplary small molecule can be separated from the equilibration buffer or process fluid via, for example, diafiltration or tangential flow filtration. In some embodiments, the analyte is the desired material to be separated from the process fluid during fluid treatment. For example, the analyte can be a large molecule such as a monoclonal antibody. Such an analyte can be desirable as, for example, it may be less likely to be considered as a "contaminant" that needs to be flushed from the chromatography system and/or the use of such an analyte does not require validation of the system.

Preferably, the analyte is selected based upon both the chromatography medium to be tested and the detection system used to detect the analyte in the wash and/or eluate. The selection of suitable analytes and detection systems for use in accordance with the invention is within the ordinary skill in the art.

For example, to determine if the membrane or monolith to be tested is positively charged, the selected analyte (that would bind to, and be subsequently eluted from, a positively charged membrane or monolith under the test conditions) is negatively charged. For testing a negatively charged membrane or monolith, the selected analyte would be positively charged. Similarly, if the membrane or monolith is to be tested to determine if it is, for example, an HIC, IMAC, HCIC, or TC membrane or monolith, the selected analyte will bind to, and be subsequently be eluted from (under the test conditions), that type of membrane or monolith.

With respect to a detection system, a UV absorbing analyte would be suitable for use with a detection system measuring the UV molar extinction coefficient.

For example, ionic molecules such as AMP (negatively charged) or adenosine (positively charged), molecules having aromatic rings and high UV molar extinction coefficients, could be used as a selected negatively charged or a selected positively charged analytes to test, respectively, a positively charged membrane, e.g., a positively charged ion-exchange membrane, or a negatively charged membrane, e.g., a negatively charged ion-exchange membrane, using a detection system measuring the UV molar extinction coefficient. Other suitable analytes having high UV molar extinction coefficients include, for example, nucleic acids (e.g., RNA and DNA), and some proteins (e.g., antibodies such as IgG).

While UV absorbing analytes are preferred, other detectable analytes, e.g., non-UV absorbing molecules, are also suitable. For example, in some embodiments, the analytes can include a detectable label, e.g., a fluorescent, chemiluminescent, or radioactive, label.

If the membrane or monolith is to be tested to determine whether it is a HIC membrane or monolith, an analyte such as a small molecule, e.g., a nucleic acid (for example an RNA such as soluble RNA, or a DNA such as plasmid DNA), or a large molecule such as a protein, for example, an immunoglobulin (e.g., IgG), a macroglobulin (e.g., $\alpha_2$-macroglobulin), an enzyme (e.g., lysozyme) could be used as the selected analyte. Other suitable analytes include, for example, bovine serum albumin (BSA), cytochrome c, and ribonuclease A.

In another illustrative example, if the membrane or monolith is to be tested to determine whether it is a HCIC membrane or monolith, an analyte such as a protein, for example, an immunoglobulin (e.g., IgG), a macroglobulin (e.g., $\alpha_2$-macroglobulin), an enzyme (e.g., lysozyme) could be used as the selected analyte. Other suitable analytes include, for example, bovine serum albumin (BSA), and cytochrome c.

In another illustrative example, if the membrane or monolith is to be tested to determine whether it is a TC membrane or monolith, an analyte such as a protein, for example, an immunoglobulin (e.g., IgG), or a macroglobulin (e.g., $\alpha_2$-macroglobulin), could be used as the selected analyte.

In yet another illustrative example, if the membrane or monolith is to be tested to determine whether it is an IMAC membrane or monolith, an analyte such as a small molecule, e.g., a nucleic acid (for example an RNA such as soluble RNA, or a DNA such as plasmid DNA), a mid-size molecule such as cytochrome c, or a large molecule such as a His-tagged protein or a poly histidine peptide could be used as the selected analyte.

The test conditions, e.g., the binding and elution conditions, solutions utilized, salt concentrations, and/or gradient(s), can be determined and carried out as is known by one of ordinary skill in the art.

While embodiments of the invention can be utilized to determine breaches of the integrity of the chromatograph device, and thus, the user can determine that the chromatography device is defective and likely unfit for its intended purpose, there may be situations where, if the results show the breach of integrity is minor, the user may determine the breach has little or no effect on the device's performance. Thus, the user may determine that the performance of the device is acceptable.

The following examples further illustrate the invention but, of course, should not be construed as in any way limiting its scope.

In each of the following examples, the detection system, that is continuously monitoring the UV signal (260 nm for nucleic acids, nucleosides and nucleotides, and 280 nm for proteins) throughout the experiments, is an OPTEK™ AF46 dual channel UV absorption detector Model 316 (optek-Danulate, Inc., Germantown, Wis.).

Example 1

This example demonstrates an embodiment of the present invention can be used to determine the integrity and chromatography type of positively charged chromatography membranes sealed in a housing.

The selected analyte, AMP, that is negatively charged, is dissolved at 3 mg/ml of 25 mM TRIS buffer (pH 8.0). 60 ml pulse AMP solutions are prepared.

The equilibration buffer is 25 mM TRIS (pH 8.0) and the elution buffer is 25 m TRIS (pH 8.0) in 1M NaCl.

A capsule filter element having 16 layers of pleated positively charged membranes (MUSTANG™ Q membranes, Pall Corporation, East Hills, N.Y.) and forming a hollow, generally cylindrical element, is sealed in a reusable stainless steel housing to provide a chromatography device.

A series of tests are carried out as described in more detail below. First, a test is carried out at a flow rate of 7.5 L/min with a device including non-punctured membranes, to provide the first (reference) pattern. Subsequently, the membranes are punctured once, and a test at the same flow rate is carried out with a device including the punctured membranes (to provide the second pattern), followed by puncturing the membranes an additional time, and testing the device again at the flow rate (to provide the third pattern).

The chromatography device is preconditioned (e.g., wetted and washed) in accordance with the filter element manufacturer's recommended protocol.

The device is equilibrated using the equilibration buffer.

A 60 ml pulse is injected into a line leading to the device, and subsequently equilibration buffer is passed through the device at the test flow rate, and continuous UV 260 nm monitoring at the outlet side of the device is maintained.

Following binding of the pulse, equilibration buffer is passed through the device at the test flow rate so that the volume equivalent from the point of pulse loading to the UV flow cell passes through the system, followed by elution buffer at the test flow rate to elute the bound analyte.

The AMP has a low charge density, and is easily eluted from the membranes.

Figure 2:
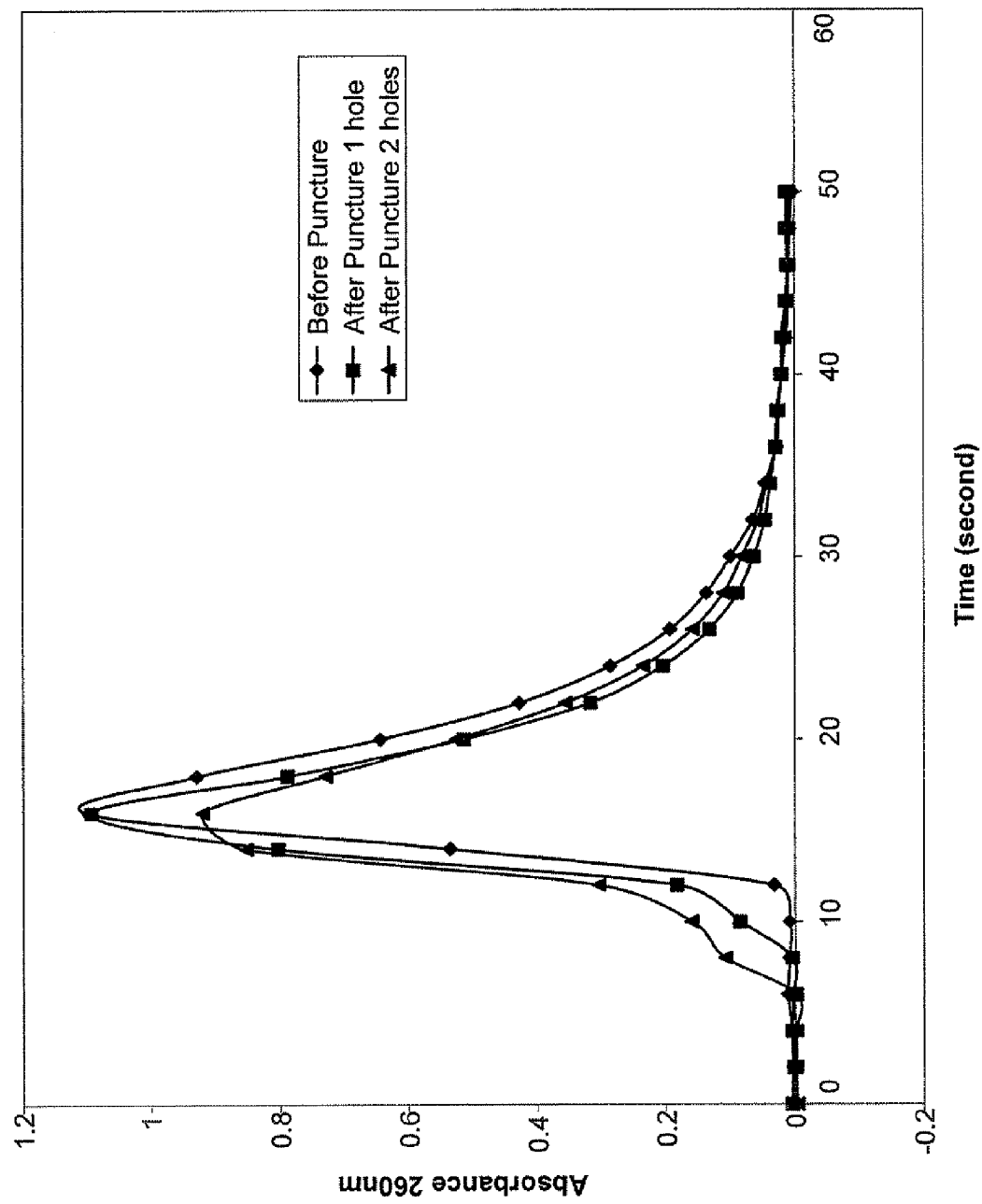
FIGS. 2 and 3 show elution patterns for membranes arranged as a filter element and sealed in a reusable housing before each test.

FIG. 2 (line with ♦) shows the reference pattern resulting from the first test.

The device is subsequently reused for additional tests, wherein the filter element is punctured before each test. Before each test, the stainless steel housing is opened, and a needle creating a 0.71 mm diameter hole is poked through all of the 16 layers. One hole is created for the first test, and an additional hole is created for the second test. After creating the hole(s), the filter element is resealed in the housing.

The device is preconditioned and tested as described above to prepare the second and third patterns (FIG. 2, lines with ■ and ▲, respectively).

The first (reference) pattern (line with ♦) shows the analyte is eluted from the integral membranes in a sharp, nearly symmetrical peak. The second and third patterns (lines with ■ and ▲) shows two peaks of the eluted analyte, an early breakthrough peak reflecting the breach of integrity, and a later peak reflecting the remainder of the pulse analyte eluted from the nonbreached portion of the membranes.

Example 2

This example shows an eluted low molecular weight analyte can be separated from the eluting fluid.

The eluate containing the analyte from Example 1 (first test) is diafiltered as follows. A MINIM™ pump station (Pall Corporation, East Hills, N.Y.) and a CENTRAMATE™ membrane cassette including OMEGA™ ultrafiltration membranes (10,000 molecular weight cut off) (Pall Corporation, East Hills, N.Y.) is set up in accordance with the manufacturer's recommended protocol. Diafiltration is performed as a constant volume operation using 10 diavolumes of 25 mM Tris-HCl (pH 8) buffer. The UV 260 nm absorbance is monitored for both the retentate and permeate. There is no detection of UV 260 nm absorbance in the retentate, and the permeate is found to have >99% of the AMP, thus showing the low molecular weight AMP is separated from the eluting fluid.

Example 3

This example demonstrates an embodiment of the present invention can be used to determine the integrity and chromatography type of positively charged chromatography membranes at three different flow rates, when the membranes are sealed in a housing.

The selected analyte, AMP, is dissolved at 3 mg/ml of 25 mM TRIS buffer (pH 8.0). 60 ml pulse AMP solutions are prepared.

The equilibration buffer is 25 mM TRIS (pH 8.0) and the elution buffer is 25 mM TRIS (pH 8.0) in 1M NaCl.

A capsule filter element having 16 layers of pleated positively charged membranes (MUSTANG™ Q membranes, Pall Corporation, East Hills, N.Y.), and forming a hollow, generally cylindrical element, is sealed in a reusable stainless steel housing to provide a chromatography device.

A series of tests are carried out as described in more detail below. First, tests are carried out at flow rates of 1.5, 5, and 7.5 L/min (separate tests) with a device including non-punctured membranes, to provide the first (reference) pattern. Subsequently, the membranes are punctured once, and tests at the three flow rates are carried out with a device including the punctured membranes (to provide the second pattern), followed by puncturing the membranes an additional time, and testing the device again at the three flow rates (to provide the third pattern).

The chromatography device is preconditioned (e.g., wetted and washed) in accordance with the filter element manufacturer's recommended protocol.

The device is equilibrated using the equilibration buffer.

A 60 ml pulse is injected into a line leading to the device, and subsequently equilibrium buffer is passed through the device at the desired flow rate (1.5, 5, and 7.5 L/min), and continuous UV 260 nm monitoring at the outlet side of the device is maintained.

Following binding of the pulse, equilibration buffer is passed through the device at the test flow rate so that the volume equivalent from the point of pulse loading to the UV flow cell passes through the system. Subsequently, elution buffer is passed through the device at the desired flow rate to elute the bound analyte.

The AMP has a low charge density, and is easily eluted from the membranes.

FIG. 3A shows the reference patterns resulting from the first tests.

The device is subsequently reused for additional tests, wherein the filter element is punctured before each test. Before each test, the stainless steel housing is opened, and a needle creating a 0.71 mm diameter hole is poked through all of the 16 layers. One hole is created for the first test, and an additional hole is created for the second test. After creating the hole(s), the filter element is resealed in the housing.

The device is preconditioned and tested as described above to prepare the second and third patterns (FIGS. 3B and 3C).

FIG. 3A shows the analyte is eluted from the integral membranes in a sharp, nearly symmetrical peak at each of the flow rates (1.5, 5, and 7.5 L/min). FIGS. 3B and 3C show two peaks of the eluted analyte at each of the flow rates, an early breakthrough peak reflecting the breach of integrity, and a later peak reflecting the remainder of the pulse analyte eluted from the nonbreached portion of the membranes. FIGS. 3B and 3C also show the breakthrough peak is more pronounced at lower flow rates, and thus, for some applications, a lower flow rate may be desirable for increasing the sensitivity of the test.

Example 4

This example demonstrates an embodiment of the present invention can be used to determine the chromatography type of negatively charged chromatography membranes sealed in a housing.

The selected analyte, adenosine, that is positively charged, is dissolved at 3 mg/ml of 10 mM acetic acid (pH 4). A 60 ml pulse adenosine solution is prepared.

The equilibration buffer is 10 mM acetic acid (pH 4) and the elution buffer is 10 mM acetic acid (pH 4) in 1M NaCl.

A capsule filter element having a filter element including 16 layers of pleated negatively charged membranes (MUSTANG™ S membranes, Pall Corporation, East Hills, N.Y.) and forming a hollow, generally cylindrical element, is sealed in a reusable stainless steel housing to provide a chromatography device.

The chromatography device is preconditioned (e.g., wetted and washed) in accordance with the filter element manufacturer's recommended protocol.

The device is equilibrated using the equilibration buffer.

A 60 ml pulse is injected into a line leading to the device, and subsequently equilibrium buffer is passed through the device at the desired flow rate of 7.5 L/min, and continuous UV 260 nm monitoring at the outlet side of the device is maintained.

Following binding of the pulse, equilibration buffer is passed through the device at the test flow rate so that the volume equivalent from the point of pulse loading to the UV flow cell passes through the system. Subsequently, elution buffer is passed through the device at the test flow rate to elute the bound analyte.

The adenosine has a low charge density, and is easily eluted from the membranes.

The absence of a detectable UV absorption peak upon washing the adenosine pulse through the device indicates liquid flows through the membranes of the capsule filter element with no bypass. The elution of bound adenosine indicates the positively charged adenosine binds to the negatively charged membranes.

Example 5

This example demonstrates an embodiment of the present invention can be used to determine the chromatography type of an immobilized metal affinity chromatography (IMAC) membrane sealed in a housing.

The selected analyte, cytochrome c (horse heart, Sigma-Aldrich Company, St. Louis, Mo.), is dissolved at 0.2 mg/ml of 10 mM Tris buffer (pH 8). A 5 ml pulse cytochrome c solution is prepared.

The equilibration buffer is 10 mM Tris buffer (pH 8), and the elution buffer is 1.0 M $NH_4Cl$ in 20 mM $NaHPO_4$ buffer at pH 7.0.

An IMAC membrane chromatography device (SARTO-BIND® IDA 75 Membrane Adsorber, Sartorius Corporation, Edgewood, N.Y.) is preconditioned (e.g., wetted and washed) and charged as the $Cu^{2+}$ form in accordance with the device manufacturer's recommended protocol.

The device is equilibrated using the equilibration buffer.

A 5 ml pulse is injected into a line leading to the device followed by equilibrium buffer at the desired flow rate of 20 mL/min, and continuous UV 280 nm monitoring at the outlet side of the device is maintained.

Following binding of the pulse, equilibration buffer is passed through the device at the test flow rate so that the volume equivalent from the point of pulse loading to the UV flow cell passes through the system. Subsequently, elution buffer is passed through the device at the test flow rate to elute the bound analyte.

The cytochrome c is easily eluted from the membranes.

The absence of a detectable UV absorption peak upon washing the cytochrome c pulse through the device indicates liquid flows through the unit's membranes with no bypass. The elution of bound cytochrome c in the elution buffer indicates the cytochrome c binds to the $Cu^{2+}$ form of the IMAC membrane.

Example 6

This example demonstrates an embodiment of the present invention can be used to determine the chromatography type of an affinity chromatography membrane sealed in a housing.

The selected analyte, polyclonal IgG, is dissolved at 1.0 mg/ml of 0.14M sodium chloride in 10 mM sodium phosphate buffer (pH 7.4). A 0.02 ml pulse polyclonal IgG solution is prepared.

The equilibration buffer is 0.14M sodium chloride in 10 mM sodium phosphate buffer (pH 7.4), and the elution buffer is 0.1M sodium citrate buffer (pH 2.5).

A Sartobind® Protein A membrane (Sartorius Corporation, Edgewood, N.Y.) is sealed in a reusable housing to provide a chromatography device.

The chromatography device is preconditioned (e.g., wetted and washed) in accordance with the filter element manufacturer's recommended protocol.

The device is equilibrated using the equilibration buffer.

A 0.02 ml pulse is injected into a line leading to the device followed by equilibrium buffer at the desired flow rate of 2 mL/min, and continuous UV 280 μm monitoring at the outlet side of the device is maintained.

Following binding of the pulse, equilibration buffer is passed through the device at the test flow rate so that the volume equivalent from the point of pulse loading to the UV flow cell passes through the system. Subsequently, elution buffer is passed through the device at the test flow rate to elute the bound analyte.

The polyclonal IgG is easily eluted from the membranes.

The absence of a detectable UV absorption peak upon washing the polyclonal IgG pulse through the device indicates liquid flows through the membranes of the capsule filter element with no bypass. The elution of bound polyclonal IgG indicates the polyclonal IgG binds to the Protein A membrane.

Example 7

This example demonstrates an embodiment of the present invention can be used to determine the integrity of a preassembled commercially available chromatography capsule and to determine the chromatography type of the positively charged chromatography membranes sealed in the housing.

The selected analyte, AMP, is dissolved at 3 mg/mL water.

The elution buffer is 25 mM TRIS (pH 8.0) in 1M NaCl.

A MUSTANG™ Q XT5000 Capsule (Pall Corporation, East Hills, N.Y.) is preconditioned (e.g., wetted and washed) in accordance with the manufacturer's recommended protocol.

The top vent valve is opened, and water is pumped through the capsule at 50 L/min. Once air has been vented from the system, the vent valve is closed and pumping continues until about 20 liters is passed through the capsule.

The pump is turned off and a 300 mL pulse of the AMP solution (3 mg/mL of water) is injected into the line at a location after the pump and before the inlet of the capsule.

The pump is turned back on at 50 L/min for about 1 minute or until sufficient time has elapsed so that a volume equivalent from the point of AMP loading to the UV flow cell passes through the system. There is little or no detectable UV260 nm signal during this step indicating that the AMP pulse has bound to the positively charged membranes.

The pump is stopped and the pump feed is switched over to the elution buffer.

The pump is turned back on at 50 L/min until the AMP pulse has been completed eluted and the UV260 nm signal returns to baseline.

The results are shown in the graph in FIG. 4. The graph shows the absence of a UV260 nm signal in the flow through process stream and the detection of a sharp peak of AMP during the elution step, thus showing the integrity of the capsule and confirming the chromatography type of the membranes.

Example 8

This example demonstrates an embodiment of the present invention can be used to determine the integrity of a sealed anion exchange radial flow monolith chromatography column sealed in a stainless steel cylindrical housing to provide a device.

The selected analyte, AMP, is dissolved at 3 mg/ml of 20 mM Tris buffer at pH 7.4.

This equilibration buffer is 20 mM Tris-HCl at pH 7.4 and the elution buffer contains 1 M NaCl in the equilibration buffer.

The column contains 8 ml of quaternary amine anion-exchange convective interactive media (CIM®QA-8 tube, Bia Separations, JM Science Inc., Grand Island, N.Y.), has a radial flow configuration and is sealed in a reusable stainless steel housing. This device is plumbed into an AKTA 100 chromatography workstation (GE Healthcare, Piscataway, N.Y.).

The sealed column is equilibrated using the equilibration buffer.

A 0.5 ml aliquot of the AMP solution is injected into a line leading to the column and subsequently equilibrium buffer is passed through the column at the desired flow rate of 16 m/min and continuous UV 260 nm monitoring at the outlet side of the device is maintained.

Following binding of the pulse, equilibration buffer is passed through the radial flow column at the test flow rate so that the volume equivalent from the point of pulse loading to the UV flow cell passes through the system. Subsequently, elution buffer is passed through the column at the test flow rate to elute the bound analyte.

The AMP has a low charge density and is easily eluted from the column.

The absence of a detectable UV absorption peak upon washing the AMP through the column indicates liquid flow through the column anion-exchange matrix resin with no bypass. The elution of bound AMP indicates the negatively charged AMP binds to the positively charged matrix resin.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for testing the integrity of a chromatography membrane sealed in a housing comprising:
    obtaining a chromatography device comprising a housing and having one or more chromatography membranes to be tested sealed in the housing;
    obtaining a selected analyte that will bind to the membrane(s) under standard binding conditions;
    placing the analyte in contact with the membrane(s) under standard binding conditions;
    eluting the analyte from the membrane(s) with an elution fluid to form an eluate containing the eluted analyte, the eluted analyte having a measurable concentration in the eluate;
    measuring a change in the concentration of the eluted analyte in the eluate over a period of time to provide an elution pattern for the tested membrane(s);
    comparing the elution pattern for the tested membrane(s) to a reference elution pattern for a membrane of known integrity; and
    determining the integrity of the tested membrane(s).

2. A method for testing the integrity of a chromatography monolith sealed in a housing comprising:
    obtaining a chromatography device comprising a housing and one or more chromatography monoliths to be tested sealed in the housing;
    obtaining a selected analyte that will bind to the monolith(s) under standard binding conditions;
    placing the analyte in contact with the monolith(s) under standard binding conditions;
    eluting the analyte from the monolith(s) with an elution fluid to form an eluate containing the eluted analyte, the eluted analyte having a measurable concentration in the eluate;
    measuring a change in the concentration of the eluted analyte in the eluate over a period of time to provide an elution pattern for the tested monolith(s);
    comparing the elution pattern for the tested monolith(s) to a reference elution pattern for a monolith of known integrity; and
    determining the integrity of the tested monolith(s).

3. A method for testing the type and integrity of a chromatography membrane sealed in a housing comprising:
    obtaining a selected analyte, the analyte being capable of binding, under standard binding conditions, to a chromatography membrane having a specified chromatography type;
    obtaining a chromatography device comprising a housing and one or more chromatography membranes to be tested sealed in the housing, the one or more chromatography membrane(s) having a chromatography type to be tested to determine whether the membrane(s) has/have the specified chromatography type;
    placing the analyte in contact with the membrane(s) under standard binding conditions wherein the analyte binds to the membrane(s) if the membrane(s) has/have the specified chromatography type;
    contacting the membrane(s) with an elution fluid to form an eluate, wherein the eluate contains the eluted analyte if the membrane(s) to be tested has/have the specified chromatography type, the eluted analyte having a measurable concentration in the eluate;
    measuring a change in the concentration of the eluted analyte in the eluate over a period of time to provide an elution pattern for the tested membrane(s);
    comparing the elution pattern for the tested membrane(s) to a reference elution pattern for a membrane of known integrity; and
    determining the integrity of the membrane(s) and whether the membrane(s) has/have the specified chromatography type.

4. A method for testing the type and integrity of a chromatography monolith sealed in a housing comprising:
    obtaining a selected analyte, the analyte being capable of binding, under standard binding conditions, to a monolith having a specified chromatography type;
    obtaining a chromatography device comprising a housing and one or more chromatography monoliths to be tested sealed in the housing, the one or more chromatography monolith(s) having a chromatography type to be tested to determine whether the monolith(s) has/have the specified chromatography type;
    placing the analyte in contact with the monolith(s) under standard binding conditions wherein the analyte binds to the monolith(s) if the monolith(s) has/have the specified chromatography type;
    contacting the monolith(s) with an elution fluid to form an eluate, wherein the eluate contains the eluted analyte if the monolith(s) to be tested has/have the specified chromatography type, the eluted analyte having a measurable concentration in the eluate; measuring a change in the concentration of the eluted analyte in the eluate over a period of time to provide an elution pattern for the tested monolith(s);

comparing the elution pattern for the tested monolith(s) to a reference elution pattern for a monolith of known integrity; and determining the integrity of the monolith(s) and whether the monolith(s) has/have the specified chromatography type.

5. The method of claim 1, including testing the chromatography type of the chromatography membrane.

6. The method of claim 2, including testing the chromatography type of the chromatography monolith.

7. The method of claim 5, wherein the chromatography type being tested is selected from the group consisting of charge, affinity, HIC, IMAC, HCIC, and TC.

8. The method of claim 5, wherein the chromatography type being tested is positively charged.

9. The method of claim 5, wherein the chromatography type being tested is negatively charged.

10. The method of claim 3, wherein the specified chromatography type is selected from the group consisting of charge, affinity, HIC, IMAC, HCIC, and TC.

11. The method of claim 3, wherein the specified chromatography type is positively charged.

12. The method of claim 3, wherein the specified chromatography type is negatively charged.

13. The method of claim 1, wherein the chromatography device includes a plurality of membranes sealed therein.

14. The method of claim 1, comprising testing the integrity of a chromatography capsule having the chromatography membrane(s) sealed therein.

15. The method of claim 1, further comprising separating the analyte in the eluate from the elution fluid.

16. The method of claim 3, wherein the chromatography device includes a plurality of membranes sealed therein.

17. The method of claim 3, comprising testing the integrity of a chromatography capsule having the chromatography membrane(s) sealed therein.

18. The method of claim 3, further comprising separating the analyte in the eluate from the elution fluid.

* * * * *